United States Patent
Lin et al.

(10) Patent No.: US 11,612,737 B2
(45) Date of Patent: Mar. 28, 2023

(54) NON-CONTACT MUSCLE SIGNAL SENSING AND ASSISTING DEVICE AND METHOD

(71) Applicant: INDUSTRIAL TECHNOLOGY RESEARCH INSTITUTE, Hsinchu (TW)

(72) Inventors: Hong-Dun Lin, Hsinchu (TW); Tai-Wei Su, Taoyuan (TW); Chun-Kai Chang, New Taipei (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 46 days.

(21) Appl. No.: 17/321,135

(22) Filed: May 14, 2021

(65) Prior Publication Data
US 2022/0233843 A1 Jul. 28, 2022

(30) Foreign Application Priority Data
Jan. 22, 2021 (TW) .................................. 110102399

(51) Int. Cl.
*A61N 1/04* (2006.01)
*A61N 1/36* (2006.01)

(52) U.S. Cl.
CPC .......... *A61N 1/0452* (2013.01); *A61N 1/0456* (2013.01); *A61N 1/36003* (2013.01); *A61N 1/36031* (2017.08)

(58) Field of Classification Search
CPC ................ A61N 1/0452; A61N 1/0456; A61N 1/36003; A61N 1/36031; A61B 5/0507;
(Continued)

(56) References Cited

U.S. PATENT DOCUMENTS 9,486,627 B1  11/2016  White
10,773,079 B2  9/2020  Keller et al.
(Continued)

FOREIGN PATENT DOCUMENTS

CN   106659892 A   5/2017
CN   111166357 A   5/2020
TW   I594786 B     8/2017

OTHER PUBLICATIONS

Taiwan Office Action dated Jul. 5, 2021 as received in application No. 110102399.

*Primary Examiner* — Carl H Layno
*Assistant Examiner* — Anh-Khoa N Dinh
(74) *Attorney, Agent, or Firm* — Maschoff Brennan

(57) ABSTRACT

A non-contact muscle signal sensing and assisting device, comprises a radar sensing module, a microprocessor and an electrical stimulation module. The radar sensing module continuously transmits a first microwave signal to a muscle bundle part and receives a corresponding reflected muscle signal, and performs a demodulation procedure on a second microwave signal and the reflected muscle signal to obtain and output a demodulated muscle signal. The microprocessor performs a muscle-movement signal characteristic processing procedure on the demodulated muscle signal to obtain a characterized muscle signal. The microprocessor obtains a muscle movement parameter according to the characterized muscle signal and controls the electrical stimulation module to emit a micro electrical stimulation signal to stimulate a reflex nerve when the muscle movement parameter fits an assistive condition, thereby stimulate muscle movement.

12 Claims, 5 Drawing Sheets

(58) Field of Classification Search
CPC ......... A61B 5/0816; A61B 5/024; A61B 5/05;
A61B 5/0205; A61B 5/113; A61B
18/1815; A61B 5/7257; A61B 5/02438;
A61B 2562/0228; A61B 5/1102; A61B
5/1116; A61B 18/18; A61B 2018/00785;
A61B 5/7207; A61B 5/021
See application file for complete search history.

(56) References Cited

U.S. PATENT DOCUMENTS

| | | |
|---|---|---|
| 2003/0073938 A1 | 4/2003 | Crawford et al. |
| 2004/0122483 A1 | 6/2004 | Nathan et al. |
| 2008/0045832 A1* | 2/2008 | McGrath ................ A61B 5/08 600/427 |
| 2013/0013026 A1 | 1/2013 | Hoyer et al. |
| 2020/0155842 A1 | 5/2020 | Lasko et al. |

* cited by examiner

NON-CONTACT MUSCLE SIGNAL SENSING AND ASSISTING DEVICE AND METHOD

CROSS-REFERENCE TO RELATED APPLICATIONS

This non-provisional application claims priority under 35 U.S.C. § 119(a) on Patent Application No(s). 110102399 filed in Republic of China (ROC) on Jan. 22, 2021, the entire contents of which are hereby incorporated by reference.

BACKGROUND

1. Technical Field

This disclosure relates to a non-contact muscle signal sensing and assisting device and method.

2. Related Art

According to statistics, stroke is not only common in middle-aged people, more and more young people with healthy living habits also suffer from stroke. Most patients may be able to regain the ability to walk after treatment, they are still likely to suffer from the sequelae of muscle weakness, which causes patients still unable to walk normally due to foot drop even after recovering from the stroke. Therefore, more and more assistive devices are developed to assist stroke patients with walking.

For example, ankle-foot orthoses (AFO) may help improve the patient's walking speed, stability and symmetry, as well as improve the patient's ability to maintain static balance. However, AFO limits the range of motion of the ankle, which in turn reduces the mobility of ankle muscle. Therefore, currently there are devices adopting functional electrical stimulation (FES) to stimulate muscle movement. However, the current devices that adopt FES do not take the inconvenience of patients operating the devices into consideration. Further, the current devices adopting FES require medical professionals to operate to provide a proper electrical stimulation.

SUMMARY

Accordingly, this disclosure provides a non-contact muscle signal sensing and assisting device and method.

According to one or more embodiment of this disclosure, a non-contact muscle signal sensing and assisting device, comprising: a radar sensing module at least comprising a microwave transmitter and a receiver, wherein the microwave transmitter continuously transmits a first microwave signal to a muscle bundle part, the receiver receives a reflected muscle signal corresponding to the first microwave signal during a movement of the muscle bundle part, and the radar sensing module performs a demodulation procedure on a second microwave signal and the reflected muscle signal to obtain and output a demodulated muscle signal; a microprocessor in signal-transmittable connection with the radar sensing module, wherein the microprocessor at least comprises an analysis module and a determination module, and the microprocessor performs a muscle-movement signal characteristic processing procedure on the demodulated muscle signal to obtain a characterized muscle signal; and an electrical stimulation module, in signal-transmittable connection with the microprocessor, and comprising an electrode, wherein the analysis module obtains a muscle movement parameter according to the characterized muscle signal, and the determination module controls the electrical stimulation module to emit a micro electrical stimulation signal to stimulate a reflex nerve when the muscle movement parameter is determined as fitting an assistive condition, to stimulate muscle movement.

According to one or more embodiment of this disclosure, a non-contact muscle signal sensing and assisting method, adapted to a radar sensing module, a microprocessor and an electrical stimulation module, the radar sensing module at least comprising a microwave transmitter and a receiver, the microprocessor at least comprising an analysis module and a determination module, the method comprising: continuously transmitting a first microwave signal, by the radar sensing module, to a muscle bundle part; receiving a reflected muscle signal, by the receiver, corresponding to the first microwave signal during a movement of the muscle bundle part; demodulating a second microwave signal and the reflected muscle signal, by the radar sensing module, to obtain and output a demodulated muscle signal; performing a muscle-movement signal characteristic processing procedure on the demodulated muscle signal to obtain a characterized muscle signal; transmitting the characterized muscle signal to the microprocessor; obtaining a muscle movement parameter, by the analysis module, according to the characterized muscle signal; and controlling the electrical stimulation module to emit a micro electrical stimulation signal, by the determination module, to stimulate a reflex nerve when the muscle movement parameter is determined as fitting an assistive condition, to stimulate muscle movement.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Figure 1:
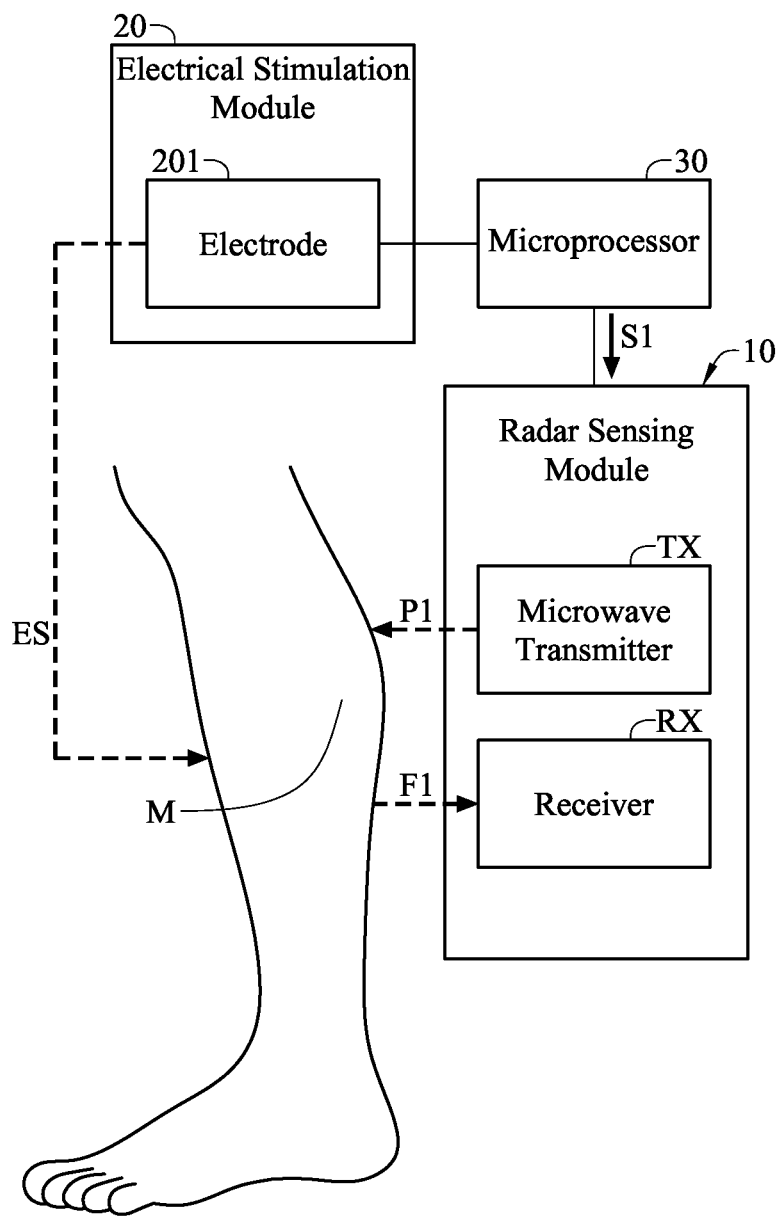
FIG. 1 is a block diagram of a non-contact muscle signal sensing and assisting device according to an embodiment of the present disclosure.

Please refer to FIG. 1, FIG. 1 is a block diagram of a non-contact muscle signal sensing and assisting device according to an embodiment of the present disclosure.

The non-contact muscle signal sensing and assisting device according to the present disclosure comprises a radar sensing module 10, an electrical stimulation module 20 and a microprocessor 30. The microprocessor 30 is in signal-transmittable connection with the radar sensing module 10 and the electrical stimulation module 20 to control the radar sensing module 10 and the electrical stimulation module 20. The radar sensing module 10 is, for example, a radar device that adopts Doppler radar mechanism to emit microwave signals and receive the reflected microwave signals. The electrical stimulation module 20 is, for example, a stimulation device that is able to emit micro electrical stimulation signal (e.g. micro-current signal). The microprocessor 30 is, for example, a processor or a controller comprising an analysis module and a determination module and is able to process and analyze signals, wherein the microprocessor 30 is preferably disposed in a personal computer or a handheld device. The present disclosure dose not limit the types of the radar sensing module 10, electrical stimulation module 20 and the microprocessor 30.

The radar sensing module 10 at least comprises a microwave transmitter TX and a receiver RX. The microwave transmitter TX is configured to continuously transmit a first microwave signal to a muscle bundle part M, and the timing of the second microwave signal P2 is later than the timing of the first microwave signal P1. The receiver RX is configured to receive a reflected muscle signal F1 corresponding to the first microwave signal P1. The muscle bundle part M may be a part of muscles, and the reflected muscle signal F1 is a signal reflected from the muscle bundle part M to the radar sensing module 10 during the movement of the muscle bundle part M, wherein the reflected muscle signal F1 is received by the receiver RX. The radar sensing module 10 performs a demodulation procedure on a second microwave signal P2 and the reflected muscle signal F1 to obtain and output a demodulated muscle signal, which will be further described below. The electrical stimulation module 20 comprises an electrode 201, and the electrode 201 is preferably a dry electrode configured to emit the micro electrical stimulation signal ES to stimulate a reflex nerve. The microprocessor 30 is in signal-transmittable connection with the radar sensing module 10 and the electrical stimulation module 20. That is, the microprocessor 30 may be electrically connected to the radar sensing module 10 and the electrical stimulation module 20, the microprocessor 30 may also be connected to the radar sensing module 10 and the electrical stimulation module 20 through Internet or Bluetooth connection, which is not limited in the present disclosure.

Further, the radar sensing module 10 and the electrical stimulation module 20 are preferably disposed together in a housing shell, and the radar sensing module 10 and the electrical stimulation module 20 preferably share a power source. In addition, the radar sensing module 10 and the microprocessor 30 may be in signal-transmittable connection with a remote device, for the remote device to display various signals obtained during the operation of the non-contact muscle signal sensing and assisting device. The remote device is, for example, a mobile device, a tablet, a laptop or a desktop computer that can present signals.

Figure 2:
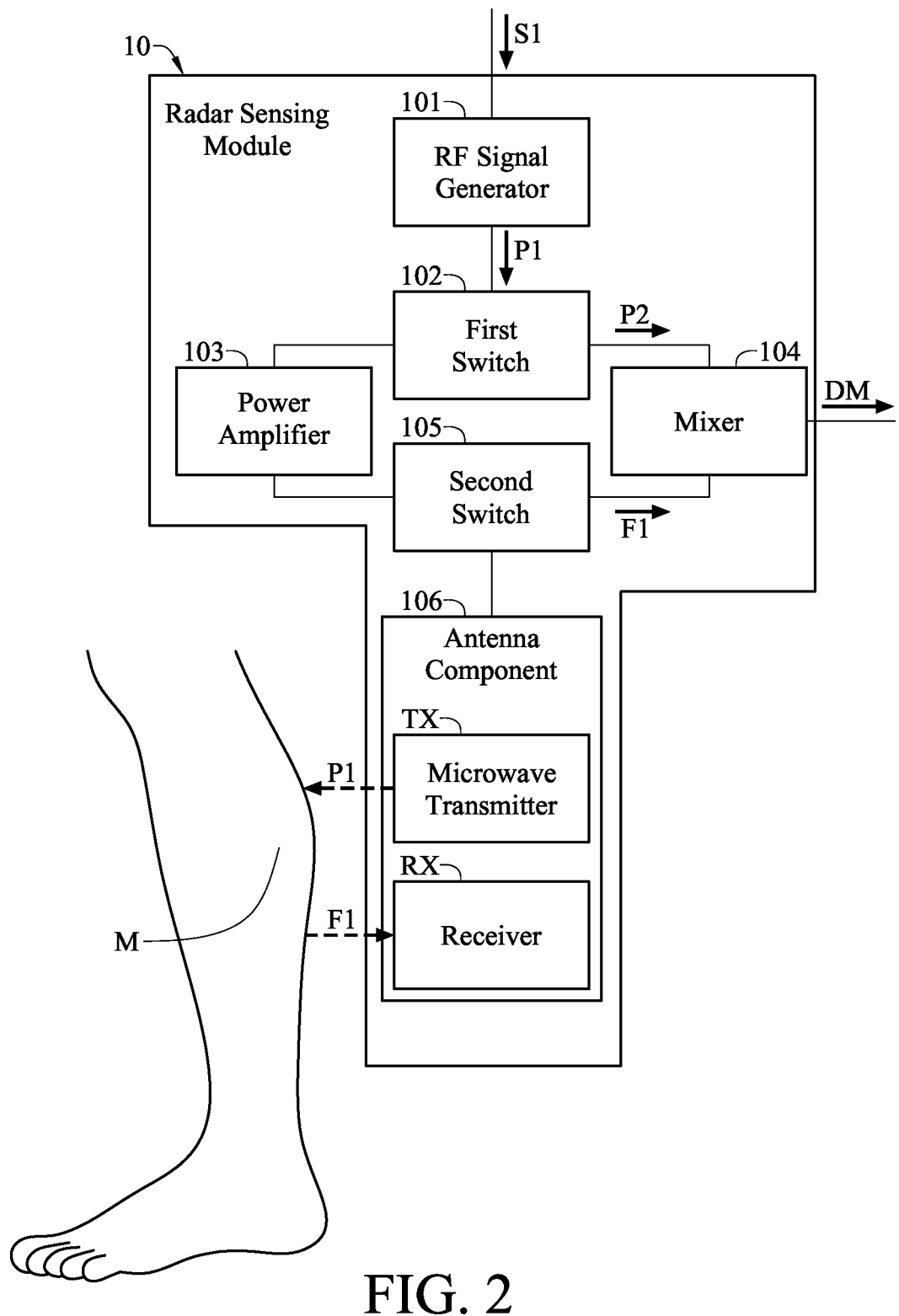
FIG. 2 is a functional block diagram of a radar sensing module according to an embodiment of the present disclosure.

Please refer to FIG. 2, wherein FIG. 2 is a functional block diagram of a radar sensing module according to an embodiment of the present disclosure. That is, FIG. 2 illustrates the functional block diagram of the radar sensing module 10 shown in FIG. 1. Specifically, the radar sensing module 10 comprises a radio frequency (RF) signal generator 101, a first switch 102, a power amplifier 103, a mixer 104, a second switch 105 and an antenna component 106, and the antenna component 106 comprises the microwave transmitter TX and the receiver RX as shown in FIG. 1. The microprocessor 30 is in signal-transmittable connection with the RF signal generator 101 and the mixer 104 of the radar sensing module 10, wherein the microprocessor 30 may comprise a pulse width modulation module to output a pulse width modulation (PWM) signal, so that the RF signal generator 101 of the radar sensing module 10 generates the first microwave signal P1 according to the PWM signal. The RF signal generator 101 generates the second microwave signal P2 according to the second period signal in the PWM signal coming from the microprocessor 30, wherein the timing of the second period signal is one period later than that of the first period signal S1 and has the same waveform as the first period signal S1

The RF signal generator 101 is connected to the first switch 102, and the first switch 102 is further connected to the power amplifier 103 and the mixer 104. The first switch 102 has a first state and a second state. When the first switch 102 is in the first state, the RF signal generator 101 is electrically connected to the power amplifier 103, and there is an open circuit between the RF signal generator 101 and the mixer 104. When the first switch 102 is in the second state, the RF signal generator 101 is electrically connected to the mixer 104, and there is an open circuit between the RF signal generator 101 and the power amplifier 103.

The power amplifier 103 is connected to the second switch 105, and the second switch 105 is further connected to the mixer 104 and the antenna component 106. The second switch 105 has a third state and a fourth state. When the second switch 105 is in the third state, the power amplifier 103 is electrically connected to the antenna component 106, and there is an open circuit between the power amplifier 103 and the mixer 104. When the second switch 105 is in the fourth state, the antenna component 106 is electrically connected to the mixer 104, and there is an open circuit between the antenna component 106 and the power amplifier 103.

Further, the radar sensing module 10 may further comprise a first low noise amplifier (not shown) and a second low noise amplifier (not shown), wherein the first low noise amplifier is connected to both the first switch 102 and the mixer 104 with the first low noise amplifier locating between the first switch 102 and the mixer 104, and the second low noise amplifier is connected to both the second switch 105 and the mixer 104 with the second low noise amplifier locating between the second switch 105 and the mixer 104. Accordingly, the second microwave signal P2 and the reflected microwave signal F1 may be amplified, and the noise generated during the simultaneous amplification of the second microwave signal P2 and the reflected muscle signal F1 may be reduced.

Figure 3:
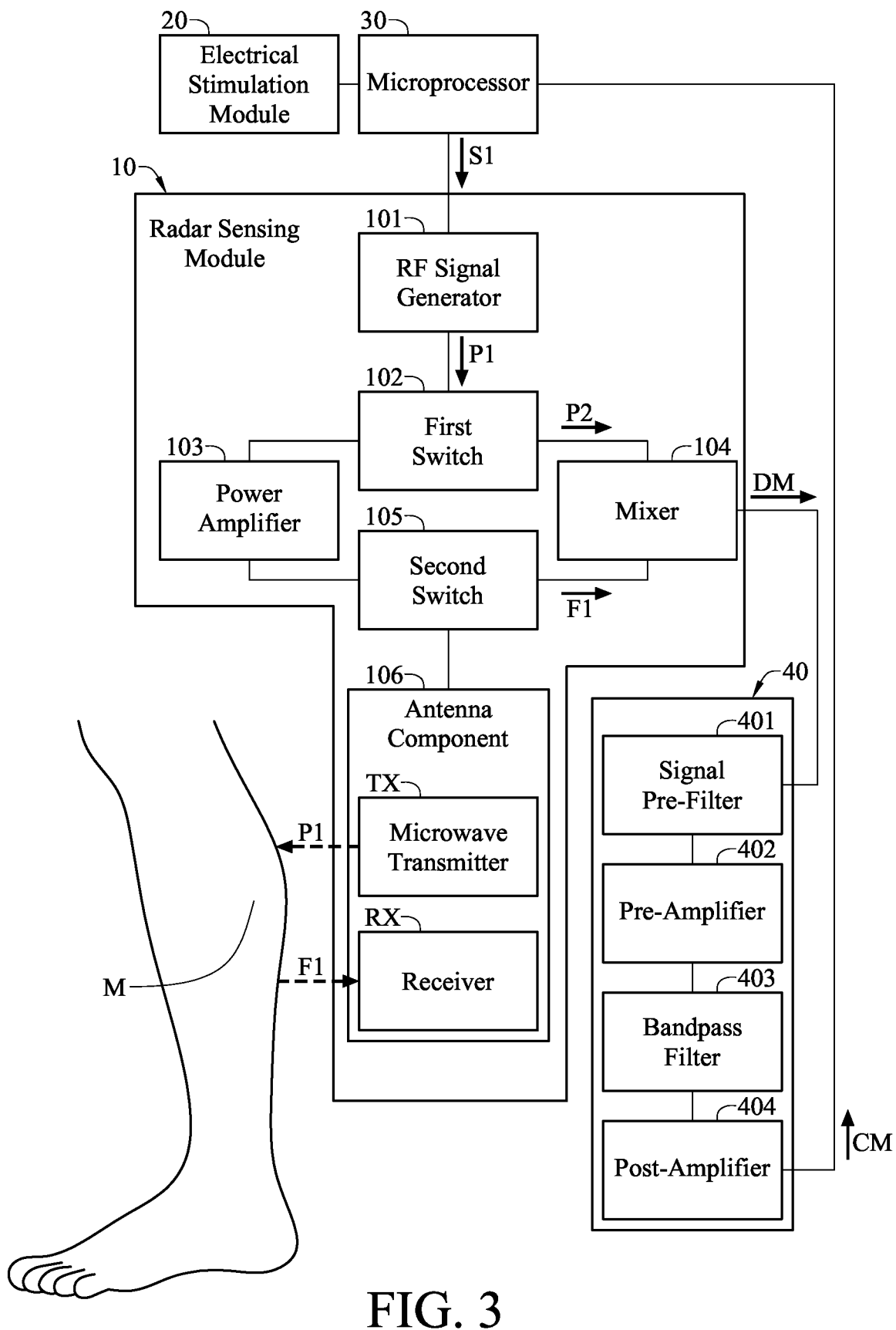
FIG. 3 is a block diagram of a non-contact muscle signal sensing and assisting device according to another embodiment of the present disclosure.

In the embodiment shown in FIG. 2, the signal outputted from the mixer 104 is transmitted to the microprocessor 30 for the microprocessor 30 to directly filter and amplify the signal outputted from the mixer 104. However, when the microprocessor 30 does not perform filtering and amplifying signal (for example, a low-cost microprocessor that is unable to perform filtering and amplification signal is deployed as the microprocessor 30 in the non-contact muscle signal sensing and assisting device of the present disclosure), a filtering and amplifying module may be disposed. Continuing from the above description, please refer to FIG. 3, FIG. 3 is a block diagram of a non-contact muscle signal sensing and assisting device according to another embodiment of the present disclosure. Comparing to FIG. 2, the non-contact muscle signal sensing and assisting device shown in FIG. 3 further comprises a filtering and amplifying module 40 configured to filter and amplify the signal outputted from the mixer 104. The filtering and amplifying module 40 comprises a signal pre-filter 401, a pre-amplifier 402, a bandpass filter 403 and a post-amplifier 404. The input terminal of the signal pre-filter 401 is connected to the output terminal of the mixer 104; the output terminal of the signal pre-filter 401 is connected to the input terminal of the pre-amplifier 402; the output terminal of the pre-amplifier 402 is connected to the input terminal of the bandpass filter 403; the output terminal of the bandpass filter 403 is connected to the input terminal of the post-amplifier 404; and the output terminal of the post-amplifier 404 is connected to the microprocessor.

In addition, the RF signal generator 101, the first switch 102, the power amplifier 103, the mixer 104 and the second switch 105 may be integrated into an integrated circuit along with the microprocessor, thereby miniaturizing the non-contact muscle signal sensing and assisting device and its radar sensing module 10.

Figure 4:
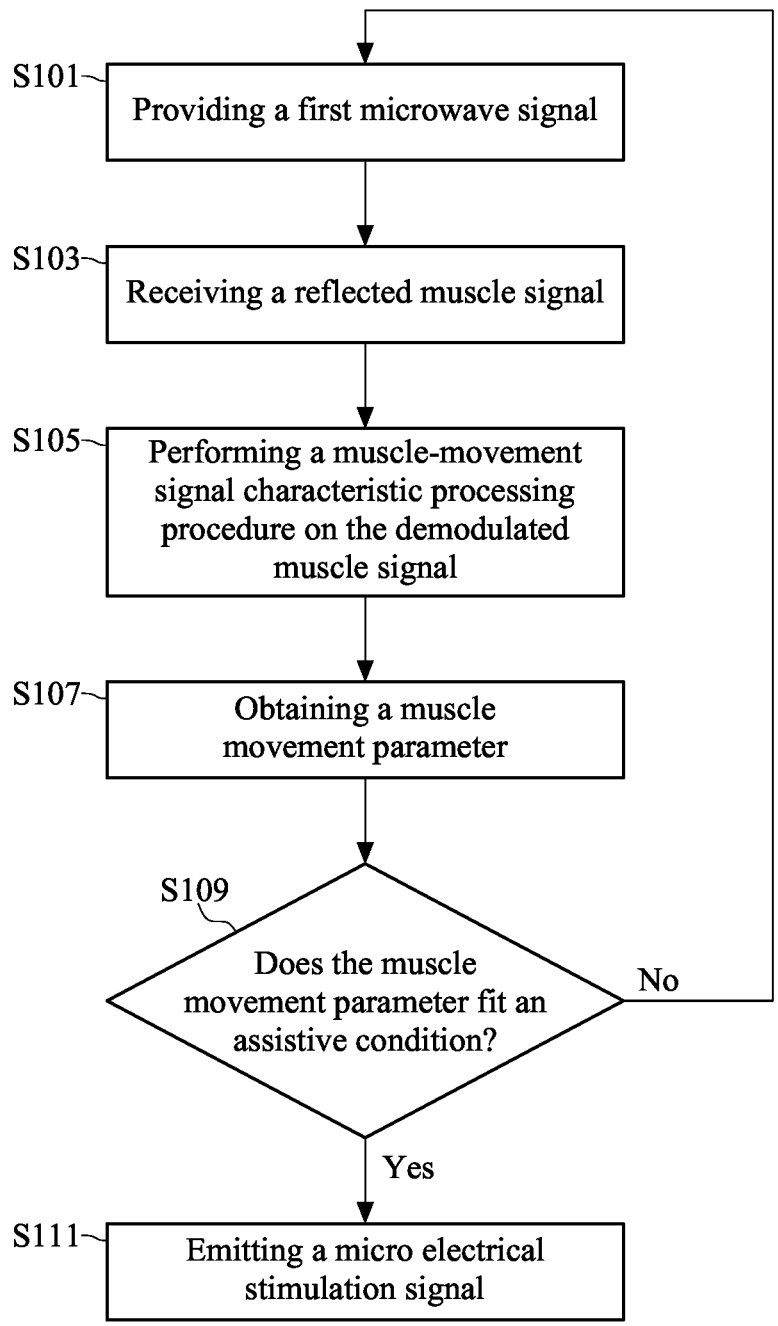
FIG. 4 is a flow chart of a non-contact muscle signal sensing and assisting method according to an embodiment of the present disclosure.

Please refer to both FIG. 3 and FIG. 4, FIG. 4 is a flow chart of a non-contact muscle signal sensing and assisting method according to an embodiment of the present disclosure.

Step S101 is: providing a microwave signal.

The microprocessor 30 controls the radar sensing module 10 continuously providing (transmitting) microwave signals to the muscle bundle part M. Specifically, when the RF signal generator 101 receives a first period signal S1 (for example, square wave signal) in the pulse width modulation (PWM) signal from the microprocessor 30, the RF signal generator 101 generates a first microwave signal P1 according to the first period signal S1. The frequency of the first microwave signal P1 is the same as that of the first period signal S1, and the waveform of the first microwave signal P1 is different from that of the first period signal S1.

When the first switch 102 receives the first microwave signal P1, the first switch 102 is in the first state, which allows the first microwave signal P1 to be transmitted to the power amplifier 103 through the first switch 102. When the first microwave signal P1 is outputted from the first switch 102, the first switch 102 switches from the first state to the second state. When the power amplifier 103 receives the first microwave signal P1, the power amplifier 103 may amplify the first microwave signal P1. Then, the power amplifier 103 outputs the amplified first microwave signal P1 to the second switch 105. When the second switch 105 receives the amplified first microwave signal P1, the second switch 105 switches to the third state, thereby transmitting the first microwave signal P1 to the antenna component 106 through the second switch 105. When the antenna component 106 receives the first microwave signal P1, the transmitter TX of the antenna component 106 is configured to transmit the first microwave signal P1 to the muscle bundle part M to measure the vibration frequency and amplitude of the muscle bundle part M. In the present embodiment, the frequency band of the first microwave signal P1 transmitted by the transmitter TX of the antenna component 106 may be 300 MHZ to 500 MHZ, but the present disclosure is not limited thereto. Since the outputted first microwave signal P1 is a microwave with short pulse and low power, the first microwave signal P1 is unlikely to cause any harm to the subject.

Step S103 is: receiving a reflected muscle signal.

The microprocessor 30 controls the receiver RX of the antenna component 106 to receive the reflected muscle signal F1 reflected from the muscle bundle part M, and the reflected muscle signal F1 is preferably the signal reflected during the movement of the muscle bundle part M. The reflected muscle signal F1 reflects the vibration frequency and amplitude of the muscle bundle part M.

After the first microwave signal P1 outputted by the antenna component 106 hits the muscle bundle part M, the reflected muscle signal F1 is reflected from the muscle bundle part M. When the receiver RX of the antenna component 106 receives the reflected muscle signal F1 from the muscle bundle part M, the antenna component 106 may transmit the reflected muscle signal F1 to the second switch 105, wherein the transmitter TX and the receiver RX have different angular position on the antenna component 106. The microprocessor 30 may modulate the time interval that the transmitter TX transmits the microwave signals, thereby allowing the receiver RX to continuously receive reflected muscle signals corresponding to different microwave signals. When the second switch 105 receives the reflected muscle signal F1, the second switch 105 switches from the third state into the fourth state, while the first switch 102 in the second state receives a second microwave signal P2 from the RF signal generator 101. The timing of the second microwave signal P2 is one period later than that of the first microwave signal P1 and has the same waveform as the first microwave signal P1. The RF signal generator 101 generates the second microwave signal P2 according to the second period signal in the PWM signal coming from the microprocessor 30, wherein the timing of the second period signal is one period later than that of the first period signal S1 and has the same waveform as the first period signal S1.

Meanwhile, the first switch 102 is in the second state and the second switch 105 is in the fourth state, and therefore, the mixer 104 receives the second microwave signal P2 and the reflected muscle signal F1 at the same time. Subsequently, the microprocessor 30 controls the mixer 104 of the radar sensing module 10 to demodulate the second microwave signal P2 and the reflected muscle signal F1 to generate a demodulated muscle signal DM associated with the muscle bundle part M.

Step S105 is: performing a muscle-movement signal characteristic processing procedure on the demodulated muscle signal.

As described above, the mixer 104 may output the demodulated muscle signal DM to the filtering and amplifying module 40 to sequentially perform a signal pre-filtering, a pre-amplifying, another filtering which is a bandpass filtering, and another amplifying which is post-amplifying on the demodulated muscle signal DM, so that the demodulated muscle signal DM is turned into a characterized muscle signal CM with the required frequency band, wherein a frequency range of the bandpass filtering is 4 Hz to 20 Hz. The post-amplifier 404 then outputs the characterized muscle signal CM to the microprocessor 30.

Step S107 is: obtaining a muscle movement parameter.

Since the demodulated muscle signal DM outputted by the mixer 104 represents the difference between the second microwave signal P2 and the reflected muscle signal F1, the characterized muscle signal CM obtained by performing filtering and amplifying on the demodulated muscle signal DM may be used to obtain parameters in a specific frequency band to acquire the information of the changes in muscle strength when the muscle bundle part M moves.

In other words, the microprocessor 30 may directly extract the surge of the characterized muscle signal CM or the muscle vibration amplitude and muscle vibration frequency of the maximum peak of wave.

Step S109 is: determining whether the muscle movement parameter fits an assistive condition.

Specifically, the determination module of the microprocessor 30 determining whether the muscle movement parameter fits the assistive condition may be: determining whether the muscle vibration amplitude falls within a movement amplitude range, and the muscle vibration frequency falls within a movement frequency range. When the determination module determines the muscle vibration amplitude falls within the movement amplitude range and the muscle vibration frequency falls within the movement frequency range, it means the muscle movement parameter fits the assistive condition, and the microprocessor 30 may control the electrode 201 of electrical stimulation module 20 to emit the low-frequency micro electrical stimulation signal ES in step S111 to stimulate the reflex nerve and stimulate muscle movement.

For example, the non-contact muscle signal sensing and assisting device according to the present disclosure is applied to assist patients with foot drop condition. Therefore, the muscle bundle part M is, for example, the gastrocnemius of the calf, and the electrical stimulation module 20 is preferably attached at the shin bone (tibia) part of the calf to allow the electrode 201 emitting the micro electrical stimulation signal ES to the peroneal nerve. In other words, the assistive condition is, for example, the muscle vibration amplitude falls within the movement amplitude range of 40 mV to 80 mV, and the muscle vibration frequency falls within the movement frequency range of 10 Hz to 20 Hz. Therefore, when the muscle vibration amplitude falls within the movement amplitude range of 40 mV to 80 mV and the muscle vibration frequency falls within the movement frequency range of 10 Hz to 20 Hz, it means the muscle bundle part M (the gastrocnemius of the calf) has tried to lift the foot, but still unable to exert its full strength, which results in the foot drop condition. Therefore, the microprocessor 30 may control the electrode 201 of electrical stimulation module 20 to emit the micro electrical stimulation signal ES, with a low frequency of 1 kHz to 10 kHz, to the peroneal nerve, in order to stimulate the movement of the muscle bundle part M.

Figure 5:
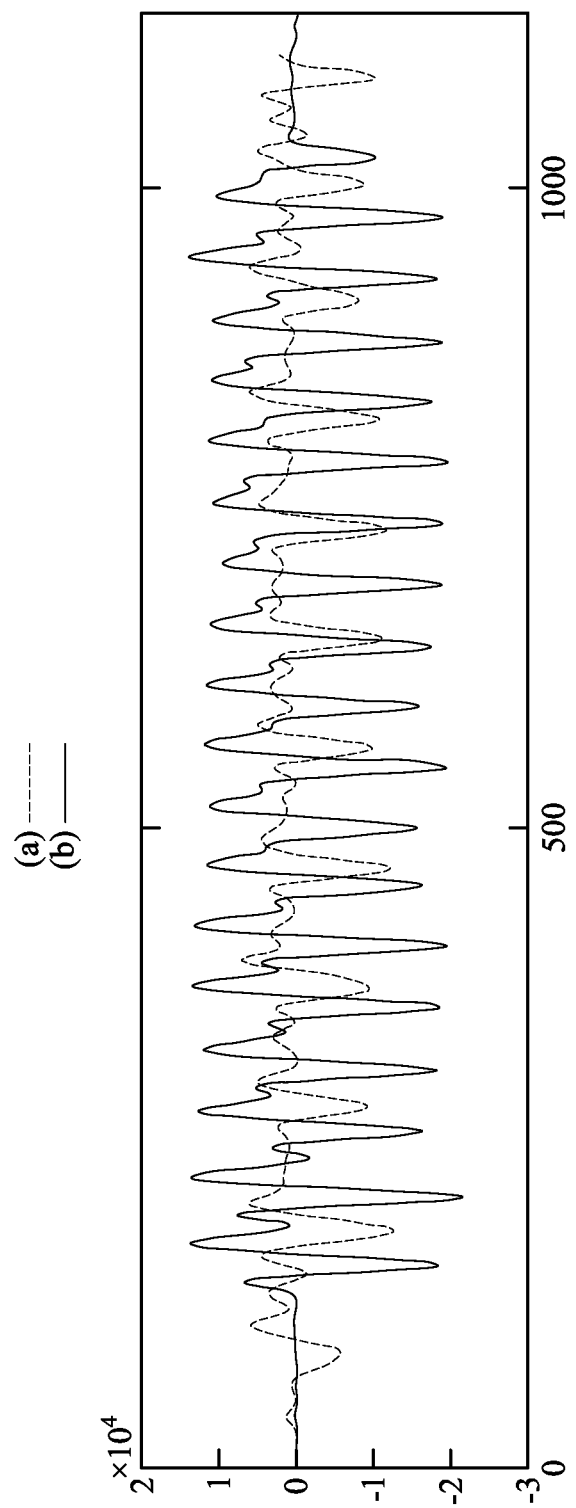
FIG. 5 illustrates diagrams of signal waveforms of (a) foot drop and (b) normal walking according to an embodiment of the present disclosure.

Please refer to FIG. 5, FIG. 5 illustrates diagrams of signal waveforms of (a) foot drop and (b) normal walking by using the non-contact muscle signal sensing and assisting device according to an embodiment of the present disclosure, wherein the unit of the horizontal axis of the waveform diagrams shown in FIG. 5 is time (milliseconds), and the unit of the vertical axis of the waveform diagrams shown in FIG. 5 is gain. The signal waveform shown in part (b) is the signal waveform detected by the non-contact muscle signal sensing and assisting device of the present disclosure during the time from the gastrocnemius exerting forces to the gastrocnemius being applied with the corresponding micro electrical stimulation signal while walking.

For patients with foot drop condition, since their gastrocnemius can't exert force normally, the legs can't be lifted fully, leading to the patient walking by dragging their feet. Therefore, as the signal (a) represented by dash line and the signal (b) represented by solid line, the signal (b), which represents normal walking, has significant higher amplitude than the amplitude of the signal (a) detected from the patients with foot drop condition. FIG. 5 shows the exercise intensity (the force exerted by the muscle) corresponding to signal (b) is significantly higher than signal (a); and the width of the wave of signal (b) is significantly narrower than that of signal (a), meaning the time of movement (the time from the foot is lifted to the foot is put down during a walking movement) is shorter than that of signal (a).

It should also be noted that, the foot drop condition described above is merely one of the applications of the non-contact muscle signal sensing and assisting device and method of the present disclosure. That is, the non-contact muscle signal sensing and assisting device and method of the present disclosure can further be applied to other conditions such as the Parkinson's disease, thereby improving the movement/exercise condition of the patient. Further, the non-contact muscle signal sensing and assisting device and method of the present disclosure may be disposed in a form of protective gear such as an over sleeve.

In view of the above description, the non-contact muscle signal sensing and assisting device and method according to one or more embodiments of the present disclosure may be easy to operate even by people without medical expertise, and may provide a proper electrical stimulation signal based on the patient's muscle exertion condition, thereby improving the patient's movement. Further, since the muscle signal may be detected without a direct contact with the skin, the patient may feel more comfortable when the non-contact muscle signal sensing and assisting device detects the muscle signals. Accordingly, by measuring the muscle signal and obtaining the corresponding frequency band of the muscle signal, the subsequent parameter analysis for the associated electrical stimulation signal may be performed more accurately.

What is claimed is:

1. A non-contact muscle signal sensing and assisting device, comprising:
   a radar sensing module at least comprising a microwave transmitter and a receiver, wherein the microwave transmitter continuously transmits a first microwave signal to a muscle bundle part, the receiver receives a reflected muscle signal corresponding to the first microwave signal during a movement of the muscle bundle part, and the radar sensing module performs a demodulation procedure on a second microwave signal and the reflected muscle signal to obtain and output a demodulated muscle signal;
   a microprocessor in signal-transmittable connection with the radar sensing module, wherein the microprocessor at least comprises an analysis module and a determination module, and the microprocessor performs a muscle-movement signal characteristic processing procedure on the demodulated muscle signal to obtain a characterized muscle signal; and
   an electrical stimulation module, in signal-transmittable connection with the microprocessor, and comprising an electrode,
   wherein the analysis module obtains a muscle movement parameter according to the characterized muscle signal, and
   the determination module controls the electrical stimulation module to emit a micro electrical stimulation signal to stimulate a reflex nerve when the muscle movement parameter is determined as fitting an assistive condition, to stimulate muscle movement.

2. The non-contact muscle signal sensing and assisting device according to claim 1, wherein the analysis module obtains the muscle movement parameter according to the characterized muscle signal by:
   extracting a muscle vibration amplitude and a muscle vibration frequency of the characterized muscle signal, and using the muscle vibration amplitude and the muscle vibration frequency as the muscle movement parameter.

3. The non-contact muscle signal sensing and assisting device according to claim 2, wherein the determination module determines the muscle movement parameter fits the assistive condition by:
   determining the muscle vibration amplitude falls within a movement amplitude range, and the muscle vibration frequency falls within a movement frequency range, wherein the movement amplitude range is from 40 mV to 80 mV, and the movement frequency range is from 10 Hz to 20 Hz.

4. The non-contact muscle signal sensing and assisting device according to claim 1, wherein the muscle-movement signal characteristic processing procedure is performing a signal pre-filtering, a pre-amplifying, a bandpass filtering and a post-amplifying on the demodulated muscle signal; wherein a frequency range of the bandpass filtering is 4 Hz to 20 Hz.

5. The non-contact muscle signal sensing and assisting device according to claim 1, wherein the radar sensing module and the electrical stimulation module share a power source.

6. The non-contact muscle signal sensing and assisting device according to claim 1, wherein the micro electrical stimulation signal is an electrical signal with a low frequency;
wherein the low frequency is 1 kHz to 10 kHz.

7. The non-contact muscle signal sensing and assisting device according to claim 1, wherein the microprocessor further comprises a pulse width modulation module, configured to output a pulse width modulation signal to the radar sensing module to generate the first microwave signal.

8. A non-contact muscle signal sensing and assisting method, adapted to a radar sensing module, a microprocessor and an electrical stimulation module, the radar sensing module at least comprising a microwave transmitter and a receiver, the microprocessor at least comprising an analysis module and a determination module, the method comprising:
continuously transmitting a first microwave signal, by the radar sensing module, to a muscle bundle part;
receiving a reflected muscle signal, by the receiver, corresponding to the first microwave signal during a movement of the muscle bundle part;
demodulating a second microwave signal and the reflected muscle signal, by the radar sensing module, to obtain and output a demodulated muscle signal;
performing a muscle-movement signal characteristic processing procedure on the demodulated muscle signal to obtain a characterized muscle signal;
transmitting the characterized muscle signal to the microprocessor;
obtaining a muscle movement parameter, by the analysis module, according to the characterized muscle signal; and
controlling the electrical stimulation module to emit a micro electrical stimulation signal, by the determination module, to stimulate a reflex nerve when the muscle movement parameter is determined as fitting an assistive condition, to stimulate muscle movement.

9. The non-contact muscle signal sensing and assisting method according to claim 8, wherein obtaining the muscle movement parameter, by the analysis module, according to the characterized muscle signal is:
extracting a muscle vibration amplitude and a muscle vibration frequency of the characterized muscle signal by the analysis module; and
using the muscle vibration amplitude and the muscle vibration frequency as the muscle movement parameter by the analysis module.

10. The non-contact muscle signal sensing and assisting method according to claim 9, wherein determining, by the determination module, the muscle movement parameter fits the assistive condition is:
determining, by the determination module, whether the muscle vibration amplitude falls within a movement amplitude range, and the muscle vibration frequency falls within a movement frequency range, wherein the movement amplitude range is from 40 mV to 80 mV, and the movement frequency range is from 10 Hz to 20 Hz; and
determining, by the determination module, the muscle movement parameter fits the assistive condition when the muscle vibration amplitude falls within the movement amplitude range, and the muscle vibration frequency falls within the movement frequency range.

11. The non-contact muscle signal sensing and assisting method according to claim 8, wherein the muscle-movement signal characteristic processing procedure comprises performing a signal pre-filtering, a pre-amplifying, a bandpass filtering and a post-amplifying on the demodulated muscle signal, wherein a frequency range of the bandpass filtering is 4 Hz to 20 Hz.

12. The non-contact muscle signal sensing and assisting method according to claim 8, wherein the micro electrical stimulation signal is an electrical signal with a low frequency;
wherein the low frequency is 1 kHz to 10 kHz.

* * * * *